(12) United States Patent
Jensen et al.

(10) Patent No.: US 7,585,294 B2
(45) Date of Patent: Sep. 8, 2009

(54) COUPLING DEVICE

(75) Inventors: Lars Bogelund Jensen, Roedovre (DK); Anette Soerensen, Kobenhavn O (DK)

(73) Assignee: Coloplast A/S, Humlebaek (DK)

( * ) Notice: Subject to any disclaimer, the term of this patent is extended or adjusted under 35 U.S.C. 154(b) by 306 days.

(21) Appl. No.: 10/532,598

(22) PCT Filed: Oct. 23, 2003

(86) PCT No.: PCT/DK03/00720

§ 371 (c)(1),
(2), (4) Date: Dec. 6, 2005

(87) PCT Pub. No.: WO2004/037339

PCT Pub. Date: May 6, 2004

(65) Prior Publication Data

US 2006/0153634 A1 Jul. 13, 2006

(30) Foreign Application Priority Data

Oct. 23, 2002 (DK) ............................. 2002 01610

(51) Int. Cl.
*A61M 25/00* (2006.01)
*A61M 3/00* (2006.01)

(52) U.S. Cl. .................. 604/523; 604/43; 128/247; 128/214.2

(58) Field of Classification Search ............. 604/523, 604/264, 93.01, 95.01, 524, 528, 530, 532, 604/533
See application file for complete search history.

(56) References Cited

U.S. PATENT DOCUMENTS

| 3,747,632 | A | | 7/1973 | Kok et al. |
| 4,256,106 | A | * | 3/1981 | Shoor .......................... 604/411 |
| 4,487,434 | A | | 12/1984 | Roche |
| 4,581,012 | A | | 4/1986 | Brown et al. |
| 4,701,159 | A | * | 10/1987 | Brown et al. ................... 604/43 |
| 5,620,427 | A | | 4/1997 | Werschmidt et al. |
| 5,651,776 | A | * | 7/1997 | Appling et al. .............. 604/534 |
| 6,428,515 | B1 | | 8/2002 | Bierman et al. |
| 2002/0115984 | A1 | | 8/2002 | Guala |
| 2002/0123786 | A1 | * | 9/2002 | Gittings et al. .............. 623/1.11 |
| 2005/0124942 | A1 | * | 6/2005 | Richmond ................... 604/246 |

FOREIGN PATENT DOCUMENTS

| DE | 37 05 339 A1 | 9/1988 |
| DE | 42 18 119 A1 | 4/1996 |
| DE | 198 33 181 C1 | 1/2000 |
| DK | PA 2002 01096 | 7/2002 |
| WO | WO 83/00812 | 3/1983 |
| WO | WO 01/34223 A1 | 5/2001 |
| WO | WO 2004/006993 A1 | 1/2004 |

\* cited by examiner

*Primary Examiner*—Nicholas D Lucchesi
*Assistant Examiner*—Ian K Holloway
(74) *Attorney, Agent, or Firm*—Jacobson Holman PLLC

(57) ABSTRACT

A coupling device including a first connector part and a second connector part each having connecting portions for engagement with corresponding connecting portions of the other connector part. A releasable locking member is provided for assisting in disengaging the engagement between the connecting portions.

20 Claims, 1 Drawing Sheet

COUPLING DEVICE

This is a nationalization of PCT/DK03/000720 filed Oct. 23, 2003 and published in English.

BACKGROUND OF THE INVENTION

1. Field of the Invention

The present invention relates to a coupling device comprising a first connector part and a second connector part, each connector part comprising at least one connecting portion for engagement with at least one corresponding connecting portion of the other connector part, a disengagement means being provided for at least assisting in disengaging the engagement between said connecting portions.

2. Description of the Related Art

Disabled persons, such as persons having a spinal cord injury or spina bifida or MS, with limited limb movement can often not perform their normal bowel function without the need for outside aids. Examples of such aids are drugs, digital stimulation, massage or colonic irrigation. Disabled persons are often unable to perform these procedures without help from another person.

One irrigation system is the arrangement disclosed in Applicant's Danish application No. PA 2002 01096, in which a reservoir is filled with irrigating liquid to a predetermined level. The reservoir is formed as a substantially sealed container and is connected with a probe for arrangement in a user by means of a conduit means.

The probe comprises a shaft portion and a fixation member for fixation in rectum in the form of an inflatable cuff. The inflatable cuff is connected with a tube for conducting an inflating medium to the cuff. The other end of the first part of the conduit means is connected with a control unit.

Generally, irrigation is carried out by inflating the cuff in order to secure the probe in position in the user, sealing against leakage, and subsequently feeding irrigating liquid from the reservoir through a tube to the probe by means of a pump.

Portability of equipment is extremely important to the user and this irrigation system may readily be transported by disabled persons. However, easy preparation of the irrigation system is also of great importance to such persons if they are to be able to use the irrigation system without aid from an assisting person.

In the irrigation system described above, the disposable probe is to be used once and subsequently discarded. Therefore, the user must connect and disconnect the probe from the two tubes leading to the control unit each time he or she uses the irrigation system. The irrigation system may e.g. be provided with two luer type connectors such as the luer locks disclosed in U.S. Pat. Nos. 6,428,515 and 5,620,427 connecting the probe with the tubes leading to the control unit.

The male luer lock connector of a single luer lock is traditionally inserted into the female luer lock connector by pressing them together and is removed by pulling and rotating the connectors in opposite directions in a wriggling motion. Disconnection by just pulling the connectors in opposite directions is normally difficult to a non-disabled person, respectively extremely difficult to a disabled person.

Therefore, as is well known in the art, an engagement means in the form of a nut or a sleeve as disclosed in U.S. Pat. No. 5,620,427 is mounted on the male luer connector, the engagement means being threaded on a corresponding engagement means disposed on the female luer lock connector, thereby enabling disconnection of the male luer lock connector from the female luer lock connector through a rotating operation that requires less strength and is more manageable than pulling the parts in opposite directions. Also, use of such engagement means facilitates connecting the luer lock connectors. Thus, by use of this method a disabled person is more likely to readily be able to connect/disconnect the probe from the tubes leading to the control unit.

However, when two tubes are arranged with small spacing as is the case in the present irrigation system, neither of the two above mentioned connecting/disconnecting methods are applicable since individual rotation of the tubes is not possible. The remaining option is to pull the connectors in opposite directions (though a small amount of wriggling could be possible) and thus, for a disabled person it is extremely difficult to connect and especially disconnect the two luer lock connectors.

From U.S. Pat. No. 3,747,632 is disclosed a multiple tubes coupling system, comprising two parts to be connected, and a ring for securing the two parts to each other's. The ring may also ease disconnection. The two parts are in the form of cylindrical portions with teeth for engaging with the ring on the surface of the portions. However, the presence of these teeth on the outer surface of the portions makes the coupling rather bulky, as well as the teeth may cling to clothes etc.

In the field of medical couplings it is often desired to have the coupling as compact as possible. However, the size of the coupling is usually dictated by the size and amount of tubes to be connected, as well as the means for connection often take up place too.

Thus, there is still a need for a coupling device having a minimum size and being easy to use.

SUMMARY OF THE INVENTION

With this background it is an object of the present invention to provide a coupling device that is easy to use.

This object is met by means of a coupling device comprising a first connector part and a second connector part, each connector part comprising at least one connecting portion for engagement with at least one corresponding connecting portion of the other connector part, a disengagement means being provided for at least assisting in disengaging the engagement between said connecting portions and each connector part, the device comprising at least two connecting portions, the disengagement means being connected with the first connector part and comprising engagement means for engagement with corresponding engagement means on the second connector part, the second connector part comprises a disk including a through-going hole in connection with each corresponding connecting portion, the engagement means of said connector part being provided on said disk, the engagement means of the disengagement means comprising internal threads and the engagement means of the second connector part comprising external threads, and wherein the holes in the disk of the second connector part are arranged with a small spacing, and in which the external threads of the engagement means of the second connector part comprise at least one recess.

By incorporating a plurality of connecting portions in each connector part, the user is able to connect and disconnect the tubes by himself or herself and thus, e.g. with the irrigation system disclosed in Applicant's Danish application No. PA 2002 01096, to perform the entire irrigation without the need for outside help.

The disengagement means is intended for connection with the first connector part and comprises engagement means for engagement with corresponding engagement means on the second connector part. The second connector part may comprise a disk including a through-going hole in connection with each corresponding connecting portion, the engagement means of said connector part being provided on said disk. The engagement means of the disengagement means may comprise internal threads corresponding to external threads of the engagement means of the second connector part. This provides for a simple and reliable operation of the coupling device, as the connector parts are pulled towards and away from each other when connecting and disconnecting the connector parts.

The through-going holes in the disk of the second connector part are arranged with a small spacing, and/or the external threads of the engagement means of the second connector part comprise at least one recess. In this way, the overall size of the coupling device may be reduced and a particularly compact design of the coupling device is achieved, which, i.a., makes the coupling device inexpensive in manufacture. However, the external threads may also not comprise any recesses.

When referring to the through-going holes of the connector part, it is obvious that these holes may have any suitable configuration according to the design of the connector portions. E.g in the case that the connector portions are in the form of a luer-lock-type coupling, the phrase "through-going holes" may cover both the male and the female portion of the coupling.

In one embodiment of the invention the external threads of the engagement means of the second connector part may comprise two or more recesses. The presence of the recesses in the external threads renders it possible to employ the recess area by having at least one of the holes extending into the recess. By dragging the holes towards the edge of the disk in the recess area the area of the disk is utilised to a maximum, and the overall size of the coupling device may be further reduced.

In a further embodiment, the engagement means comprises a bayonet coupling including at least one track in the disengagement means and at least one projection on the second connector part, said at least one track including at least one portion extending obliquely with respect to the axial direction of the disengagement means.

In another embodiment, at least some of said connecting portions have such an axial extension that the first and the second connector parts are brought into connection with each other before activation of the disengagement means, thus, engaging in a loose connection, allowing the user to let go of the disengagement means and subsequently get a firmer grip of the disengagement means, the purpose being to enable the user to more readily rotate the disengagement means to connect and/or disconnect the first connector part with the second connector part.

In yet another embodiment, the disengagement means comprises handle means to ease the rotating operation of the disengagement means when connecting the first connector part with the second connector part and during the disconnecting operation.

In a further embodiment, the first connector part comprises two male luer lock connecting portions and the second connector part comprises two female luer lock connecting portions.

In another embodiment, each connector part may be provided with more than two connecting portions. Furthermore, the disengagement means may be mounted on the second connector part, and the design of the connecting portions may be varied, as it is e.g. conceivable to have one female and one male luer lock connector on each connector part.

In another aspect of the invention, a probe incorporating the first or the second connector part of a coupling device is provided. Either the male or the female luer lock connector may be attached to the probe.

In yet another aspect of the invention, a method of disengaging the engagement between a first and a second connector part of a coupling device is provided.

Other features and advantages will readily be appreciated from the following description of examples of embodiments.

BRIEF DESCRIPTION OF THE DRAWINGS

In the following the invention will be described in further detail with reference to the schematic drawings, in which.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
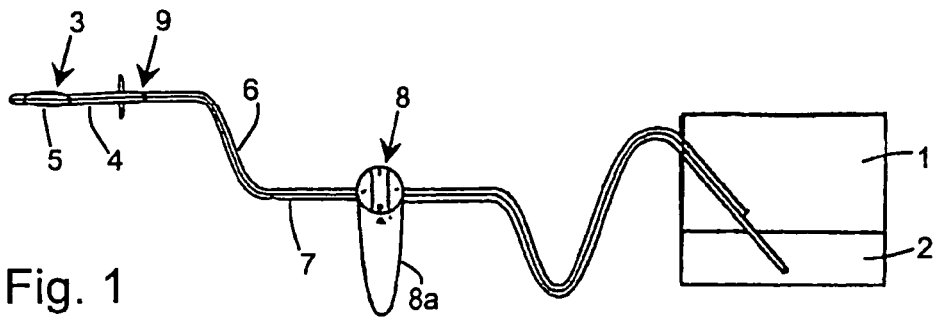
FIG. 1 shows an irrigation system, which is not as such a part of the invention, incorporating a probe and a coupling device according to the present invention.

In FIG. 1, an irrigation system is shown, in which a reservoir 1 is filled with irrigating liquid 2 to a predetermined level. The reservoir 1 is formed as a substantially sealed container and is connected with a probe 3 for arrangement in a user by means of a conduit means in a manner that will be described in further detail in the following.

The probe 3 comprises a shaft portion 4 and a fixation member in the form of an inflatable cuff 5. The inflatable cuff 5 is connected with a tube 6 for conducting an inflating medium to the cuff. The probe 3 is furthermore connected with a tube 7 for conducting irrigating liquid. The other ends of the first tubes 6, 7 are connected with a control unit 8. Generally, irrigation is carried out by inflating the cuff 5 in order to secure the probe 3 in position in the user, and subsequently feeding irrigating liquid 2 from the reservoir 1 to the probe 3 by means of a pump 8a.

Figure 2:
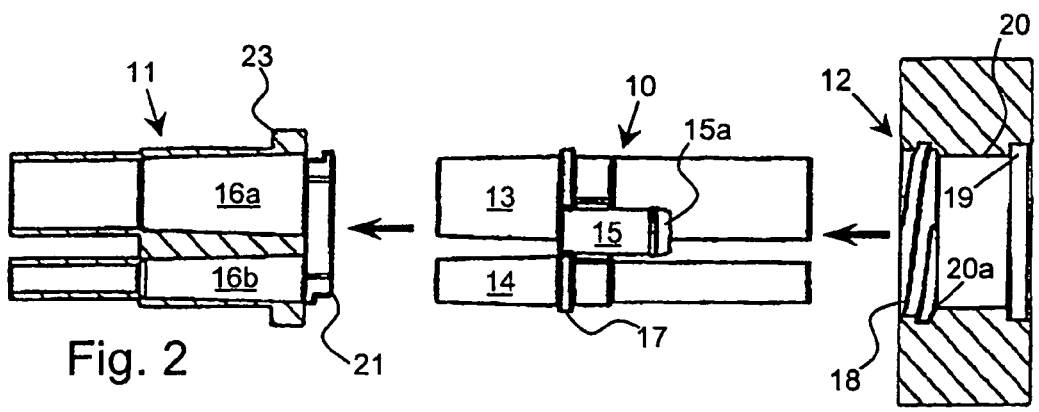
FIG. 2 is an exploded sectional view of an embodiment of a coupling device according to the present embodiment.

FIG. 2 shows an embodiment of the coupling device 9 comprising a first connector part 10, a second connector part 11, and a disengagement means 12 or releasable locking member. The coupling device 9 connects the probe 3 with the gas conducting tube 6 and the liquid conducting tube 7. In this embodiment of the present invention, the first connector part 10 is provided with two tapered conical portions 13, 14, whereas the second connector part is provided with two corresponding tapered bores 16a, 16b. The connecting portions, i.e. the portions 13, 14 and the bores 16a, 16b may be conical as suggested in the embodiments shown in the drawings, or they may be non-circular, e.g. polygonal, in section. Also, they may have a constant or a varying cross-section and they may have arched as well as rectilinear engagement surfaces. In the present embodiment, the portions 13, 14 and the bores 16a, 16b together constitute two luer lock connectors for connecting the probe 3 with the tubes 6, 7.

Figure 3:
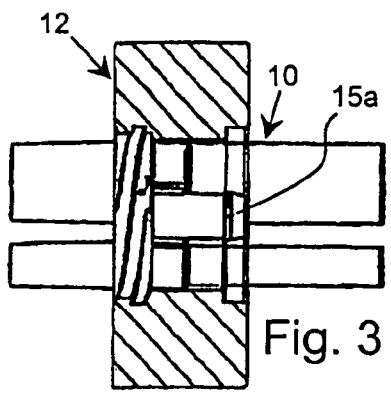
FIG. 3 is a sectional view of a disengagement means attached to a first connector part.

FIG. 3 shows the disengagement means or releasable locking member 12 attached to the first connector part 10. Before use of the coupling device 9, the disengagement means or releasable locking member 12 in the form of a sleeve or a nut is mounted on the first connector part 10. The disengagement means or releasable locking member 12 is kept in place on the first connector part 10 with respect to movement along the longitudinal axis of and is rotatably mounted about such longitudinal axis by means of a shoulder portion 17 and a resilient member 15 in such a way that the disengagement means or releasable locking member 12 engages with the first connector part 10 by moving the disengagement means or releasable locking member 12 in the direction shown in FIG. 2, the disengagement means or releasable locking member 12 sliding over a projection 15a of the resilient member 15, the projection 15a of the resilient member 15 being pushed slightly inwards during this movement, and, subsequently, the projection 15a moving outwards into engagement with a stepped portion 19 of the disengagement means or releasable locking member 12. At the opposite end of the disengagement means or releasable locking member 12, an engagement structure 18 is provided between a central portion 20 and the end of the disengagement means or releasable locking member 12. The engagement structure 18 of the disengagement means or releasable locking member 12 has such dimensions that a step 20a is formed at the transition to the central portion 20. The step 20a abuts on the shoulder portion 17 on the first connector part 10. In the present embodiment, the engagement structure 18 of the releasable locking member 12 is provided in the form of internal threads 18.

Figure 3A:
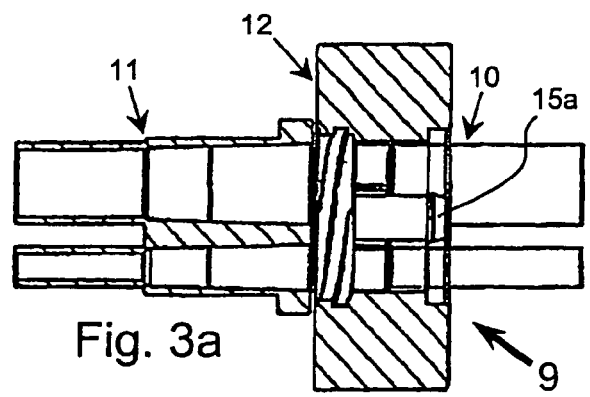
FIG. 3a is a sectional view of an assembled coupling device.

FIG. 3a shows the assembled coupling device 9.

Figure 4:
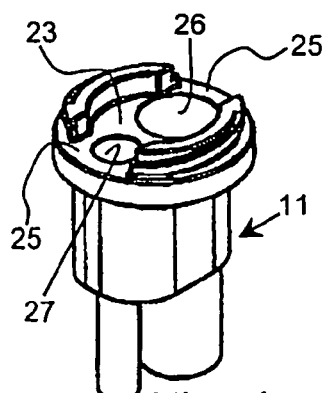
FIG. 4 is a perspective view of a second connector part.

FIG. 4 is a perspective view of the second connector part 11. In the present embodiment, a disk 23 disposed at the end of the second connector part 11 facing the first connector part 10 has a circular shape, thereby allowing the attachment of a second engagement structure 21 to also have a circular shape. Therefore, engagement structures can be implemented through which a rotatable and consequently much less physically demanding mounting of the first connector part 10 on and dismounting of this connector part from the second connector part 11 is possible.

Holes 26, 27 are provided in the circular disk 23 of the second connector part 11 in order to enable flow through the coupling device 9. In the embodiment of FIG. 4, the holes 26, 27 are arranged with a small spacing, e.g. less than 10%, preferably 7% or less of the diameter of the disk (i.a. dependent on the thickness of the tube walls), and furthermore a recess 25 is disposed in the engagement structure 21 of the second connector part 11 to make room for the holes 26, 27. This provides the advantage of a reduction in size of the circular disk 23 of the second connector part resulting in an overall smaller size of the coupling device 9.

Figure 5:
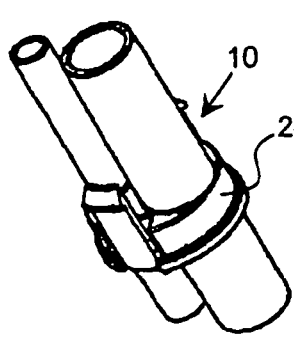
FIG. 5 is a perspective view of the first connector part.
Figure 6:
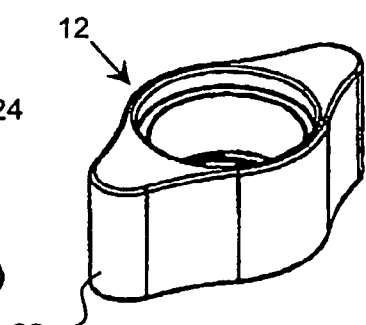
FIG. 6 is a perspective view of the disengagement means.

FIG. 5 is a perspective view of the first connector part 10, whereas FIG. 6 is a perspective view of the disengagement means or releasable locking member 12. Similar to the second connector part 11, a circular disk 24 is provided at the end of the first connector part 10 facing the second connector part 11, allowing the mounting and rotation of the also circular releasable locking member 12 on the first connector part 10.

When the releasable locking member 12 is attached to the first connector part 10, the engagement structure 18 of the releasable locking member 12 corresponds to engagement structure 21 of the second connector part 11. In the present embodiment, the engagement structure 21 of the second connector part 11 is provided in the form of external threads 21. In an embodiment (not shown), the engagement structure of the second connector part 11 and the releasable locking member 12 is provided in the form of a bayonet coupling, e.g. including one track portion extending obliquely with respect to the axial direction of the releasable locking member and a projection, e.g in the form of a pin member on the second connector part.

Thus, when connecting the first connector part 10 with the second connector part 11, the connection portions on the first connector part 10 engage into the second connector part 11 through a rotating operation of the releasable locking member, thereby allowing the connecting portions 13, 14 of the first connector part 10 to more readily be properly connected and/or disconnected with the connecting portions 16a, 16b of the second connector part 11.

In the embodiment shown in the drawings, the releasable locking member 12 is provided with a handle 22 to ease the rotating operation of the releasable locking member 12 when connecting the first connector part 10 with the second connector part 11 and during the disconnecting operation.

Alternatively, the first connector part 10 and the second connector part 11 may be initially brought together before engagement of the engagement structure 21 of the first connector part in the engagement structure 21 of the second connector part, the first connector part 10 and the second connector part 11 thus engaging in a loose connection, allowing the user to let go of the releasable locking member 12 and subsequently get a firmer grip of the releasable locking member 12, the purpose being to enable the user to more readily rotate the releasable locking member to connect and/or disconnect the first connector part 10 with the second connector part 11.

The invention should not be regarded as being limited to the embodiment shown and described in the above description but various modifications may be carried out without departing from the scope of the claims.

For instance, each connector part may be provided with more than two connecting portions. Furthermore, the releasable locking member may be mounted on the second connector part, and the design of the connecting portions may be varied, as it is e.g. conceivable to have one female and one male luer lock connector on each connector part. Also, either the male or the female luer lock connector may be attached to the probe 3.

The connecting portions 16a, 16b, 13, 14 are not necessarily of a luer lock type, they may instead include two disks, each with two holes and further, each hole may be enclosed by sealing members. In such a design, the holes may be pushed together and sealed by activating the releasable locking member.

Alternatively, the releasable locking member 12 is e.g. applied only when disconnecting the first connector part 10 from the second connector part 11. Thus, the first connector part 10 and the second connector part 11 may be engaged into each other by just pushing the two connector parts 10, 11 into each other, without activating the engagement structures 21, 18. However, as in the embodiments described above, the first connector part 10 and the second connector part 11 are disengaged by activating the releasable locking member. This alternative provides for a faster assembly of the coupling device 9, the user still being able to readily disengage the first connector part 10 from the second connector part 11.

As a further alternative, the releasable locking member may be formed integrally with the first or the second connector part, e.g. as an arm hingedly connected with the first or the second connector part and comprising a hook section engaging the other connector part. By activating the arm, the first and the second connector parts are substantially pulled out of each other.

Furthermore, the coupling device 9 is not limited to use in the coupling between the probe 3 and the tubes 6, 7 but may also be applied in other couplings of the irrigation system, e.g. in the coupling between the tubes and the control unit or between the tubes and the reservoir.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A coupling device comprising a first connector part and a second connector part, each connector part including at least one connecting portion configured to engage with at least one corresponding connecting portion of the other connector part to connect said first and second connector parts in substantially linear alignment with one another, a releasable locking member configured to assist in disengaging the engagement between said connecting portions, said releasable locking member having a first engagement structure and being secured to the first connector part in a fixed position relative to a longitudinal axis of said first connector part while being rotatably movable about said first connector part at said fixed position, said second connector part having a disk with a through-going hole in communication with each corresponding connecting portion, respectively, and a second engagement structure on said disk, said first and second engagement structures being complementary to one another to engage through respective rotational movement thereof about said longitudinal axis to lock the connection between said first and second connector parts against separation in response to longitudinally directed force in an absence of respective counter-rotational movement of said first and second engagement structures.

2. The coupling device as set forth in claim 1, wherein the disk of the second connector part has two holes arranged with a small spacing.

3. The coupling device as set forth in claim 1, wherein the first engagement structure of said releasable locking member includes internal threads, and the second engagement structure of the second connector part includes external threads.

4. The coupling device as set forth in claim 3, wherein the external threads include at least one recess.

5. The coupling device as set forth in claim 3, wherein the external threads include two or more recesses.

6. The coupling device as set forth in claim 4, wherein at least one of the through-going holes extends into the recess.

7. The coupling device as set forth in claim 1, wherein the engagement structures include a bayonet coupling having at least one track in the releasable locking member and at least one projection on the second connector part, said at least one track including at least one portion extending obliquely with respect to an axial direction of the releasable locking member.

8. The coupling device as set forth in claim 1, wherein at least some of said connecting portions have an axial extension such that the first and the second connector parts are brought into connection with each other before activation of the releasable locking member.

9. The coupling device as set forth in claim 3, wherein said releasable locking member includes a handle.

10. The coupling device as set forth in claim 1, wherein the first connector part includes two male luer lock connecting portions and the second connector part includes two female luer lock connecting portions.

11. The coupling device as set forth in claim 1, wherein said first connector part or said second connector part is associated with a probe for an irrigation system.

12. A coupling device comprising a first connector part and a second connector part, said first connector part including two male luer lock connecting portions configured to engage with two female luer lock connecting portions of the second connector part to connect said first and second connector parts in substantially linear alignment with one another through axial movement, a releasable locking member configured to assist in disengaging the engagement between said connecting portions, said releasable locking member having a first engagement structure and being secured to the first connector part in a fixed axial position thereon while being rotatably movable about said first connector part, said second connector part having a transversely extending disk with a second engagement structure thereon, said first and second engagement structures being complementary to one another to engage through respective rotational movement thereof to lock the connection between said first and second connector parts against separation in response to axial force.

13. The coupling device as set forth in claim 12, wherein said disk has a through-going hole in communication with each corresponding connecting portion.

14. The coupling device as set forth in claim 12, wherein the disk of the second connector part has two through-going holes in communication with each corresponding connecting portion, said holes being arranged with a small spacing.

15. The coupling device as set forth in claim 14, wherein the first engagement structure of said releasable locking member includes internal threads, and the second engagement structure of the second connector part includes external threads.

16. The coupling device as set forth in claim 15, wherein the external threads include at least one recess.

17. The coupling device as set forth in claim 15, wherein the external threads include two or more recesses.

18. The coupling device as set forth in claim 16, wherein at least one of the through-going holes extends into the recess.

19. The coupling device as set forth in claim 12, wherein at least some of said connecting portions have an axial extension such that the first and the second connector parts are brought into connection with each other before activation of the releasable locking member.

20. The coupling device as set forth in claim 12, wherein said releasable locking member includes a handle.

* * * * *

UNITED STATES PATENT AND TRADEMARK OFFICE
CERTIFICATE OF CORRECTION

PATENT NO. : 7,585,294 B2
APPLICATION NO. : 10/532598
DATED : September 8, 2009
INVENTOR(S) : Jensen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this

Fourteenth Day of September, 2010

David J. Kappos
*Director of the United States Patent and Trademark Office*